(12) United States Patent
Caparso et al.

(10) Patent No.: US 11,420,063 B2
(45) Date of Patent: Aug. 23, 2022

(54) SYSTEMS AND METHODS TO IMPROVE SLEEP DISORDERED BREATHING USING CLOSED-LOOP FEEDBACK

(71) Applicant: XII Medical, Inc., Cleveland, OH (US)

(72) Inventors: Anthony V. Caparso, North Ridgeville, OH (US); Josh Nickols, Louisville, KY (US)

(73) Assignee: XII MEDICAL, INC., Cleveland, OH (US)

( * ) Notice: Subject to any disclaimer, the term of this patent is extended or adjusted under 35 U.S.C. 154(b) by 4 days.

(21) Appl. No.: 16/866,488

(22) Filed: May 4, 2020

(65) Prior Publication Data

US 2020/0346016 A1 Nov. 5, 2020

Related U.S. Application Data

(60) Provisional application No. 62/841,978, filed on May 2, 2019.

(51) Int. Cl.
*A61N 1/36* (2006.01)
*A61N 1/05* (2006.01)
(Continued)

(52) U.S. Cl.
CPC ....... *A61N 1/36139* (2013.01); *A61N 1/0548* (2013.01); *A61N 1/3611* (2013.01);
(Continued)

(58) Field of Classification Search
None
See application file for complete search history.

(56) References Cited

U.S. PATENT DOCUMENTS

| | | |
|---|---|---|
| 4,990,160 A | 2/1991 | Terino |
| 5,591,216 A | 1/1997 | Testerman et al. |

(Continued)

FOREIGN PATENT DOCUMENTS

| | | |
|---|---|---|
| JP | 2013-208182 A | 10/2013 |
| WO | 1992/19318 A1 | 11/1992 |

(Continued)

OTHER PUBLICATIONS

Bailey, E. Fiona. "Activities of human genioglossus motor units." Respiratory physiology & neurobiology 179.1 (2011): 14-22.
(Continued)

*Primary Examiner* — Ankit D Tejani
(74) *Attorney, Agent, or Firm* — Fortem IP LLP; Katrina Marcelo; Mary Fox (57) ABSTRACT

Neural stimulation is provided according to a closed loop algorithm to treat sleep disordered breathing (SDB), including obstructive sleep apnea (OSA). The closed loop algorithm is executed by a system comprising a processor (which can be within the neural stimulator). The closed loop algorithm includes monitoring physiological data (e.g., EMG data) recorded by a sensor implanted adjacent to an anterior lingual muscle; identifying a trigger within the physiological data, wherein the trigger is identified as a biomarker for a condition related to sleep (e.g., inspiration); and applying a rule-based classification (which can learn) to the trigger to determine whether one or more parameters of a stimulation should be altered based on the biomarker.

23 Claims, 5 Drawing Sheets

(51) Int. Cl.
  *A61N 1/372* (2006.01)
  *A61B 5/11* (2006.01)
  *A61B 5/00* (2006.01)
  *A61B 5/394* (2021.01)

(52) U.S. Cl.
  CPC ......... *A61N 1/37229* (2013.01); *A61B 5/1114* (2013.01); *A61B 5/1116* (2013.01); *A61B 5/394* (2021.01); *A61B 5/4552* (2013.01); *A61B 5/4812* (2013.01); *A61B 5/4818* (2013.01); *A61N 1/37211* (2013.01)

(56) References Cited

U.S. PATENT DOCUMENTS

| | | | |
|---|---|---|---|
| 5,609,621 A | 3/1997 | Bonner |
| 5,716,377 A | 2/1998 | Rise et al. |
| 5,877,466 A | 3/1999 | Bolongeat-Mobleu et al. |
| 5,988,171 A | 11/1999 | Sohn et al. |
| 6,240,316 B1 | 5/2001 | Richmond et al. |
| 6,587,725 B1 | 7/2003 | Durand et al. |
| 6,770,022 B2 | 8/2004 | Mechlenburg et al. |
| 7,660,632 B2 | 2/2010 | Kirby et al. |
| 7,668,591 B2 | 2/2010 | Lee et al. |
| 7,711,438 B2 | 5/2010 | Lattner et al. |
| 7,885,713 B2 | 2/2011 | Campbell et al. |
| 8,255,056 B2 | 8/2012 | Tehrani |
| 8,498,712 B2 | 7/2013 | Bolea et al. |
| 8,498,713 B2 | 7/2013 | McClure et al. |
| 8,574,164 B2 | 11/2013 | Mashiach |
| 8,577,464 B2 | 11/2013 | Mashiach |
| 8,577,465 B2 | 11/2013 | Mashiach |
| 8,577,466 B2 | 11/2013 | Mashiach |
| 8,577,467 B2 | 11/2013 | Mashiach et al. |
| 8,577,468 B2 | 11/2013 | Mashiach et al. |
| 8,577,472 B2 | 11/2013 | Mashiach et al. |
| 8,577,478 B2 | 11/2013 | Mashiach et al. |
| 8,577,647 B2 | 11/2013 | Farritor et al. |
| 8,585,617 B2 | 11/2013 | Mashiach et al. |
| 8,588,941 B2 | 11/2013 | Mashiach |
| 8,626,304 B2 | 1/2014 | Bolea et al. |
| 8,644,957 B2 | 2/2014 | Mashiach |
| 8,700,183 B2 | 4/2014 | Mashiach |
| 8,718,776 B2 | 5/2014 | Mashiach et al. |
| 8,744,589 B2 | 6/2014 | Bolea et al. |
| 8,751,005 B2 | 6/2014 | Meadows et al. |
| 8,798,773 B2 | 8/2014 | Mashiach |
| 8,812,113 B2 | 8/2014 | Mashiach |
| 8,812,135 B2 | 8/2014 | Mashiach |
| 8,831,730 B2 | 9/2014 | Mashiach et al. |
| 8,838,256 B2 | 9/2014 | Mashiach et al. |
| 8,897,880 B2 | 11/2014 | Mashiach |
| 8,897,895 B2 | 11/2014 | Mashiach |
| 8,903,493 B2 | 12/2014 | Mashiach et al. |
| 8,903,515 B2 | 12/2014 | Mashiach |
| 8,948,871 B2 | 2/2015 | Mashiach et al. |
| 8,958,893 B2 | 2/2015 | Mashiach |
| 8,989,868 B2 | 3/2015 | Mashiach et al. |
| 9,031,653 B2 | 5/2015 | Mashiach |
| 9,031,654 B2 | 5/2015 | Meadows et al. |
| 9,044,612 B2 | 6/2015 | Mashiach et al. |
| 9,061,151 B2 | 6/2015 | Mashiach et al. |
| 9,061,162 B2 | 6/2015 | Mashiach et al. |
| 9,095,725 B2 | 8/2015 | Mashiach |
| 9,101,774 B2 | 8/2015 | Mashiach et al. |
| 9,155,899 B2 | 10/2015 | Mashiach et al. |
| 9,186,511 B2 | 11/2015 | Bolea |
| 9,220,907 B2 | 12/2015 | Mashiach et al. |
| 9,220,908 B2 | 12/2015 | Mashiach |
| 9,248,290 B2 | 2/2016 | Mashiach |
| 9,248,291 B2 | 2/2016 | Mashiach |
| 9,248,302 B2 | 2/2016 | Mashiach et al. |
| 9,259,585 B2 | 2/2016 | Vajha et al. |
| 9,302,093 B2 | 4/2016 | Mashiach |
| 9,308,370 B2 | 4/2016 | Lima et al. |
| 9,308,381 B2 | 4/2016 | Mashiach et al. |
| 9,314,613 B2 | 4/2016 | Mashiach |
| 9,314,641 B2 | 4/2016 | Meadows et al. |
| 9,327,132 B2 | 5/2016 | Mashiach |
| 9,339,651 B2 | 5/2016 | Meadows et al. |
| 9,358,392 B2 | 6/2016 | Mashiach |
| 9,370,657 B2 | 6/2016 | Tehrani et al. |
| 9,393,435 B2 | 7/2016 | Mashiach |
| 9,403,009 B2 | 8/2016 | Mashiach |
| 9,403,025 B2 | 8/2016 | Mashiach et al. |
| 9,409,013 B2 | 8/2016 | Mashiach et al. |
| 9,415,215 B2 | 8/2016 | Mashiach |
| 9,415,216 B2 | 8/2016 | Mashiach |
| 9,421,372 B2 | 8/2016 | Mashiach et al. |
| 9,463,318 B2 | 10/2016 | Mashiach et al. |
| 9,486,628 B2 | 11/2016 | Christopherson et al. |
| 9,757,560 B2 | 9/2017 | Papay |
| 9,849,288 B2 | 12/2017 | Meadows et al. |
| 9,950,166 B2 | 4/2018 | Mashiach et al. |
| 10,029,098 B2 | 7/2018 | Papay |
| 10,065,038 B2 | 9/2018 | Papay |
| 10,105,538 B2 | 10/2018 | Bolea et al. |
| 10,238,468 B2 | 3/2019 | Forsell |
| 10,675,467 B2 | 6/2020 | Papay |
| 2002/0010495 A1 | 1/2002 | Freed et al. |
| 2004/0122787 A1* | 6/2004 | Avinash ............. G16H 50/20 706/50 |
| 2006/0224211 A1 | 10/2006 | Durand et al. |
| 2007/0160274 A1 | 7/2007 | Mashiach |
| 2007/0263915 A1 | 11/2007 | Mashiach |
| 2008/0260217 A1 | 10/2008 | Mashiach |
| 2008/0260229 A1 | 10/2008 | Mashiach |
| 2009/0082831 A1 | 3/2009 | Paul et al. |
| 2009/0226057 A1 | 9/2009 | Mashiach et al. |
| 2009/0270960 A1 | 10/2009 | Zhao et al. |
| 2010/0094379 A1 | 4/2010 | Meadows et al. |
| 2010/0179562 A1 | 7/2010 | Linker et al. |
| 2010/0241195 A1 | 9/2010 | Meadows et al. |
| 2010/0260217 A1 | 10/2010 | Redford |
| 2010/0280568 A1 | 11/2010 | Bulkes et al. |
| 2010/0292769 A1 | 11/2010 | Brounstein et al. |
| 2011/0071606 A1 | 3/2011 | Kast et al. |
| 2011/0093036 A1 | 4/2011 | Mashiach |
| 2011/0125212 A1 | 5/2011 | Tyler |
| 2011/0230702 A1 | 9/2011 | Honour |
| 2012/0010532 A1 | 1/2012 | Bolea et al. |
| 2013/0085537 A1 | 4/2013 | Mashiach |
| 2013/0085558 A1 | 4/2013 | Mashiach |
| 2013/0204097 A1 | 8/2013 | Rondoni et al. |
| 2013/0289401 A1 | 10/2013 | Colbaugh et al. |
| 2014/0031840 A1 | 1/2014 | Mashiach |
| 2014/0031902 A1 | 1/2014 | Mashiach |
| 2014/0031903 A1 | 1/2014 | Mashiach |
| 2014/0031904 A1 | 1/2014 | Mashiach |
| 2014/0046221 A1 | 2/2014 | Mashiach et al. |
| 2014/0052219 A1 | 2/2014 | Mashiach et al. |
| 2014/0100642 A1 | 4/2014 | Mashiach |
| 2014/0135868 A1 | 5/2014 | Bashyam |
| 2014/0172061 A1 | 6/2014 | Mashiach |
| 2014/0266933 A1 | 9/2014 | Andersen et al. |
| 2014/0358026 A1 | 12/2014 | Mashiach et al. |
| 2014/0358189 A1 | 12/2014 | Mashiach et al. |
| 2014/0358196 A1 | 12/2014 | Mashiach |
| 2014/0358197 A1 | 12/2014 | Mashiach et al. |
| 2014/0371802 A1 | 12/2014 | Mashiach et al. |
| 2014/0371817 A1 | 12/2014 | Mashiach et al. |
| 2014/0379049 A1 | 12/2014 | Mashiach et al. |
| 2015/0032177 A1 | 1/2015 | Mashiach et al. |
| 2015/0073232 A1 | 3/2015 | Ahmad et al. |
| 2015/0077308 A1 | 3/2015 | Jeon et al. |
| 2015/0088025 A1 | 3/2015 | Litvak et al. |
| 2015/0096167 A1 | 4/2015 | Zhao et al. |
| 2015/0112402 A1 | 4/2015 | Mashiach |
| 2015/0112416 A1 | 4/2015 | Mashiach et al. |
| 2015/0142120 A1 | 5/2015 | Papay |
| 2015/0224307 A1 | 8/2015 | Bolea |
| 2015/0265221 A1 | 9/2015 | Flanagan et al. |
| 2015/0283313 A1 | 10/2015 | Huber |
| 2015/0290454 A1 | 10/2015 | Tyler et al. |
| 2015/0290465 A1 | 10/2015 | Mashiach |

(56) References Cited

U.S. PATENT DOCUMENTS

| | | |
|---|---|---|
| 2015/0343221 A1 | 12/2015 | Mashiach |
| 2016/0094082 A1 | 3/2016 | Ookawa et al. |
| 2016/0106976 A1 | 4/2016 | Kucklick |
| 2016/0121121 A1 | 5/2016 | Mashiach |
| 2016/0121122 A1 | 5/2016 | Mashiach |
| 2016/0175587 A1 | 6/2016 | Lima et al. |
| 2016/0184583 A1 | 6/2016 | Meadows et al. |
| 2016/0235990 A1 | 8/2016 | Mashiach |
| 2016/0346537 A1 | 12/2016 | Mashiach |
| 2017/0087360 A1 | 3/2017 | Scheiner |
| 2017/0106190 A1 | 4/2017 | Papay |
| 2017/0128002 A1* | 5/2017 | Christopherson .. A61B 5/14542 |
| 2017/0143230 A1 | 5/2017 | Kent et al. |
| 2017/0274210 A1 | 9/2017 | Papay |
| 2017/0290699 A1 | 10/2017 | Radmand |
| 2017/0296815 A1 | 10/2017 | Papay |
| 2018/0015282 A1 | 1/2018 | Waner et al. |
| 2018/0028324 A1 | 2/2018 | Pivonka et al. |
| 2018/0117313 A1 | 5/2018 | Schmidt et al. |
| 2018/0191069 A1 | 7/2018 | Chen et al. |
| 2018/0200512 A1 | 7/2018 | Bolea et al. |
| 2018/0221673 A1 | 8/2018 | Kuang |
| 2019/0151656 A1 | 5/2019 | Bolea et al. |
| 2019/0160282 A1 | 5/2019 | Dieken et al. |
| 2019/0247664 A1 | 8/2019 | Irazoqui et al. |
| 2020/0016401 A1 | 1/2020 | Papay et al. |
| 2020/0254249 A1* | 8/2020 | Rondoni ............ A61N 1/36139 |
| 2020/0269044 A1 | 8/2020 | Papay |
| 2020/0346010 A1 | 11/2020 | Papay et al. |
| 2020/0346017 A1 | 11/2020 | Caparso et al. |
| 2020/0346024 A1 | 11/2020 | Caparso et al. |
| 2021/0106824 A1 | 4/2021 | Caparso et al. |
| 2021/0128914 A1 | 5/2021 | Papay |

FOREIGN PATENT DOCUMENTS

| | | | |
|---|---|---|---|
| WO | 2005/018737 A1 | 3/2005 | |
| WO | WO-2007/080579 A2 | 7/2007 | |
| WO | WO-2007/080579 A3 | 7/2007 | |
| WO | WO-2007/080580 A2 | 7/2007 | |
| WO | WO-2007/080580 A3 | 7/2007 | |
| WO | WO-2008/129545 A1 | 10/2008 | |
| WO | WO-2009/007896 A2 | 1/2009 | |
| WO | WO-2009/007896 A3 | 1/2009 | |
| WO | WO-2009/109971 A2 | 9/2009 | |
| WO | WO-2009/109971 A3 | 9/2009 | |
| WO | 2009/143560 A1 | 12/2009 | |
| WO | WO-2010/006218 A2 | 1/2010 | |
| WO | WO-2010/006218 A3 | 1/2010 | |
| WO | WO-2011/048590 A1 | 4/2011 | |
| WO | WO-2011/077433 A1 | 6/2011 | |
| WO | 2013057597 A1 | 4/2013 | |
| WO | WO-2013/046032 A2 | 4/2013 | |
| WO | WO-2013/046032 A3 | 4/2013 | |
| WO | WO-2013/046035 A2 | 4/2013 | |
| WO | WO-2013/046035 A3 | 4/2013 | |
| WO | WO-2013/046038 A2 | 4/2013 | |
| WO | WO-2013/046038 A3 | 4/2013 | |
| WO | WO-2013/046039 A2 | 4/2013 | |
| WO | WO-2013/046039 A3 | 4/2013 | |
| WO | WO-2013/046040 A2 | 4/2013 | |
| WO | WO-2013/046040 A3 | 4/2013 | |
| WO | WO-2013/046042 A2 | 4/2013 | |
| WO | WO-2013/046042 A3 | 4/2013 | |
| WO | WO-2013/046043 A2 | 4/2013 | |
| WO | WO-2013/046043 A3 | 4/2013 | |
| WO | WO-2013/046044 A2 | 4/2013 | |
| WO | WO-2013/046044 A3 | 4/2013 | |
| WO | WO-2013/046048 A2 | 4/2013 | |
| WO | WO-2013/046048 A3 | 4/2013 | |
| WO | WO-2013/046049 A2 | 4/2013 | |
| WO | WO-2013/046049 A3 | 4/2013 | |
| WO | WO-2013/046053 A2 | 4/2013 | |
| WO | WO-2013/046053 A3 | 4/2013 | |
| WO | WO-2013/057594 A2 | 4/2013 | |
| WO | WO-2013/057594 A3 | 4/2013 | |
| WO | WO-2013/061164 A2 | 5/2013 | |
| WO | WO-2013/061164 A3 | 5/2013 | |
| WO | WO-2013/061169 A2 | 5/2013 | |
| WO | WO-2013/061169 A3 | 5/2013 | |
| WO | 2013/177621 A1 | 12/2013 | |
| WO | WO-2014/016684 A2 | 1/2014 | |
| WO | WO-2014/016684 A3 | 1/2014 | |
| WO | WO-2014/016686 A2 | 1/2014 | |
| WO | WO-2014/016686 A3 | 1/2014 | |
| WO | WO-2014/016687 A2 | 1/2014 | |
| WO | WO-2014/016687 A3 | 1/2014 | |
| WO | WO-2014/016688 A2 | 1/2014 | |
| WO | WO-2014/016688 A3 | 1/2014 | |
| WO | WO-2014/016691 A2 | 1/2014 | |
| WO | WO-2014/016691 A3 | 1/2014 | |
| WO | WO-2014/016692 A2 | 1/2014 | |
| WO | WO-2014/016692 A3 | 1/2014 | |
| WO | WO-2014/016693 A2 | 1/2014 | |
| WO | WO-2014/016693 A3 | 1/2014 | |
| WO | WO-2014/016694 A2 | 1/2014 | |
| WO | WO-2014/016694 A3 | 1/2014 | |
| WO | WO-2014/016697 A2 | 1/2014 | |
| WO | WO-2014/016697 A3 | 1/2014 | |
| WO | WO-2014/016700 A2 | 1/2014 | |
| WO | WO-2014/016700 A3 | 1/2014 | |
| WO | WO-2014/016701 A2 | 1/2014 | |
| WO | WO-2014/016701 A3 | 1/2014 | |
| WO | 2014/047310 A1 | 3/2014 | |
| WO | WO-2014/049448 A2 | 4/2014 | |
| WO | WO-2014/049448 A3 | 4/2014 | |
| WO | WO-2014/057361 A2 | 4/2014 | |
| WO | WO-2014/057361 A3 | 4/2014 | |
| WO | WO-2014/096969 A2 | 6/2014 | |
| WO | WO-2014/096969 A3 | 6/2014 | |
| WO | WO-2014/096971 A1 | 6/2014 | |
| WO | WO-2014/096973 A2 | 6/2014 | |
| WO | WO-2014/096973 A3 | 6/2014 | |
| WO | WO-2014/207576 A2 | 12/2014 | |
| WO | WO-2014/207576 A3 | 12/2014 | |
| WO | WO-2015/004540 A2 | 1/2015 | |
| WO | WO-2015/004540 A3 | 1/2015 | |
| WO | 2015077283 A1 | 5/2015 | |
| WO | WO-2015/139053 A1 | 9/2015 | |
| WO | WO-2017/173433 A1 | 10/2017 | |
| WO | 2020223723 A1 | 11/2020 | |
| WO | 2020223740 A1 | 11/2020 | |
| WO | 2021076188 A1 | 4/2021 | |

OTHER PUBLICATIONS

PCT International Search Report and Written Opinion for corresponding International Application Serial No. PCT/US2020/031383, dated Oct. 9, 2020, pp. 1-17.

PCT International Search Report and Written Opinion for corresponding International Application Serial No. PCT/US2020/031389, dated Sep. 8, 2020, pp. 1-12.

Bjorninen, T. et al. (2009). "The effect of fabrication method on passive UHF RFID tag performance," International Journal of Antennas and Propagation, vol. 2009, Article ID 920947, pp. 1-8.

Cienfuegos et al., Mandible—Surgical approach—Intraocular—AO Surgery Reference, v1 .0 Dec. 1, 2008—(Accessed Apr. 18, 2016).

Cienfuegos et al., Mandible—Surgical approach—Submental—AO Surgery Reference, v1 .0 Dec. 1, 2008—(Accessed Apr. 18, 2016).

European Office Action corresponding to EP Application No. 14 809 219.0, dated May 2, 2017, 4 pages.

Final Office Action dated Jan. 10, 2017, for U.S. Appl. No. 14/547,400, filed Nov. 19, 2014, 14 pages.

Final Office Action dated Jun. 20, 2018, for U.S. Appl. No. 15/618,199, filed Jun. 9, 2017, 10 pages.

Final Office Action dated Apr. 23, 2019, for U.S. Appl. No. 15/618,199, filed Jun. 9, 2017, 9 pages.

Final Office Action dated Oct. 23, 2020, for U.S. Appl. No. 16/865,668, filed May 4, 2020, 14 pages.

Final Office Action dated Dec. 22, 2020, for U.S. Appl. No. 16/865,541, filed May 4, 2020, 16 pages.

(56) References Cited

OTHER PUBLICATIONS

Final Office Action dated Feb. 7, 2018, for U.S. Appl. No. 15/341,039, filed Nov. 2, 2016, 16 pages.
Final Office Action dated Aug. 17, 2021, for U.S. Appl. No. 16/865,668, filed May 4, 2020, 7 pages.
Final Office Action dated Jul. 27, 2021, for U.S. Appl. No. 16/507,390, filed Jul. 10, 2019, 13 pages.
Final Office Action dated Oct. 15, 2021, for U.S. Appl. No. 16/865,541, filed May 4, 2020, 18 pages.
Final Office Action dated Nov. 22, 2021, for U.S. Appl. No. 16/865,363, filed May 3, 2020, 9 pages.
International Search Report and Written Opinion dated Feb. 10, 2015, for PCT Application No. PCT/US2014/066311, filed on Nov. 19, 2014, 8 pages.
International Search Report and Written Opinion dated Sep. 7, 2020, for PCT Application No. PCT/US2020/031266, filed on May 4, 2020, 10 pages.
International Search Report and Written Opinion dated Aug. 14, 2020, for PCT Application No. PCT/US2020/031279, filed on May 4, 2020, 19 pages.
Non-Final Office Action dated Apr. 26, 2016, for U.S. Appl. No. 14/547,400, filed Nov. 19, 2014, 12 pages.
Non-Final Office Action dated Aug. 10, 2017, for U.S. Appl. No. 15/341,039, filed Nov. 2, 2016, 14 pages.
Non-Final Office Action dated Jan. 24, 2018, for U.S. Appl. No. 15/618,199, filed Jun. 9, 2017, 10 pages.
Non-Final Office Action dated Jan. 18, 2019, for U.S. Appl. No. 15/618,199, filed Jun. 9, 2017, 9 pages.
Non-Final Office Action dated Sep. 26, 2019, for U.S. Appl. No. 15/618,199, filed Jun. 9, 2017, 13 pages.
Non-Final Office Action dated Jun. 24, 2020, for U.S. Appl. No. 16/865,541, filed May 4, 2020, 14 pages.
Non-Final Office Action dated Jan. 26, 2018. for U.S. Appl. No. 15/639,300, filed Jun. 30, 2017, 14 pages.
Non-Final Office Action dated Jan. 14, 2021, for U.S. Appl. No. 16/507,390, filed Jul. 10, 2019, 11 pages.
Non-Final Office Action dated Apr. 16, 2021, for U.S. Appl. No. 16/865,668, filed May 4, 2020, 8 pages.
Non-Final Office Action dated May 11, 2021, for U.S. Appl. No. 16/865,363, filed May 3, 2020, 10 pages.
Non-Final Office Action dated Jun. 24, 2021, U.S. Appl. No. 16/865,541, filed May 4, 2020, 17 pages.
Non-Final Office Action dated Jul. 15, 2021, for U.S. Appl. No. 16/870,292, filed May 8, 2020, 5 pages.
Non-Final Office Action dated Dec. 3, 2021, for U.S. Appl. No. 16/865,668, filed May 4, 2020, 9 pages.
Notice of Allowance dated May 17, 2017, for U.S. Appl. No. 14/547,400, filed Nov. 19, 2014, 6 pages.
Notice of Allowance dated Apr. 5, 2018, for U.S. Appl. No. 15/341,039, filed Nov. 2, 2016, 9 pages.
Notice of Allowance dated Jan. 29, 2020, for U.S. Appl. No. 15/618,199, filed Jun. 9, 2017, 8 pages.
Notice of Allowance dated May 10, 2018, for U.S. Appl. No. 15/639,300, filed Jun. 30, 2017, 8 pages.
Notice of Allowance dated Nov. 19, 2021, for U.S. Appl. No. 16/866,523, filed May 4, 2020, 8 pages.
Schwartz, A.R. et al. (1996). "Electrical stimulation of the lingual musculature in obstructive sleep apnea," Journal of Applied Physiology 81:643-652.
International Search Report and Written Opinion dated Apr. 22, 2022, International Application No. PCT/US2022/070101, 15 pages.
International Search Report and Written Opinion dated Aug. 14, 2020, International Application No. PCT/US2020/031279, 19 pages.

\* cited by examiner

SYSTEMS AND METHODS TO IMPROVE SLEEP DISORDERED BREATHING USING CLOSED-LOOP FEEDBACK

CROSS-REFERENCE TO RELATED APPLICATIONS

This application claims priority to U.S. Provisional Application Ser. No. 62/841,978, filed May 2, 2019, entitled "Systems and Methods for treating Obstructive Sleep Apnea." The entirety of this provisional application is hereby incorporated by reference for all purposes.

TECHNICAL FIELD

The present disclosure relates generally to systems and methods for treating sleep disordered breathing (SDB) and, more particularly, to systems and methods for providing neural stimulation delivered in a physiological manner and adjusted based on biomarkers that are input into a closed loop algorithm to treat SDB, including obstructive sleep apnea (OSA).

BACKGROUND

Upper airway sleep disorders (UASDs) are conditions that occur in the upper airway that diminish sleep time and sleep quality, resulting in patients exhibiting symptoms that include daytime sleepiness, tiredness and lack of concentration. Obstructive sleep apnea (OSA), a type of UASD, is characterized by cessation of airflow because of upper airway obstruction despite simultaneous respiratory effort. The respiratory effort continues despite obstruction until the individual is aroused from sleep. During sleeping the genioglossus muscle and other muscles that hold the airway patent relax, causing the mandible and the tongue to move posteriorly, which decreases upper airway volume. The obstruction causes a decrease in oxygen blood level, leading to increased respiratory drive and this cycle continues until the patient is aroused.

OSA is highly prevalent, affecting one in five adults in the United States. One in fifteen adults has moderate to severe OSA requiring treatment. OSA is the most common type of sleep apnea. Untreated OSA results in reduced quality of life measures and increased risk of disease including hypertension, stroke, heart disease, etc. Continuous positive airway pressure (CPAP) is a standard treatment for OSA. While CPAP is non-invasive and highly effective, it is not well tolerated by patients and has several side effects. Patient compliance and/or tolerance for CPAP is often reported to be between 40% and 60%. Surgical treatment options for OSA, such as anterior tongue muscle repositioning, orthognathic bimaxillary advancement, uvula-palatal-pharyngoplasty, and tracheostomy are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibular advancement), and/or they may be socially stigmatic (e.g., tracheostomy) and have extensive morbidity.

SUMMARY

The present disclosure relates generally to systems and methods for treating sleep disordered breathing (SDB) and, more particularly, to systems and methods for providing neural or neuromuscular stimulation delivered in a physiological manner and adjusted based on biomarkers that are input into a closed loop algorithm to improve SDB, including obstructive sleep apnea (OSA).

One aspect of the present disclosure relates to a system that provides neural stimulation according to a closed loop algorithm to treat SDB. The system includes one or more sensors, a computing device, and one or more electrodes. In some instances, the sensors, computing device, and/or the electrodes can be part of a neural stimulation device. The sensor(s) can be implantable adjacent to an anterior lingual muscle and configured to record physiological data. The computing device can include a non-transitory memory storing instructions; and a processor to access the non-transitory memory and analyze, decode and execute the instructions to at least: monitor the physiological data recorded by the sensor; identify a trigger within the physiological data, wherein the trigger is identified as a biomarker for a condition related to sleep; and apply a rule-based classification to the trigger to determine whether one or more parameters of a stimulation signal should be altered based on the biomarker. The electrode(s) can be implantable adjacent to a neural or muscular target site, such the hypoglossal nerve, and configured to deliver stimulation to the target site during a period and to alter the one or more parameters of the stimulation in response to a signal from the computing device.

Another aspect of the present disclosure relates to a method for providing neural stimulation according to a closed loop algorithm to treat SDB, including OSA. The method can include steps that can be executed by a system comprising a processor. The steps include: monitoring physiological data recorded by a sensor implanted adjacent to an anterior lingual muscle; identifying a trigger within the physiological data, wherein the trigger is identified as a biomarker for a condition related to sleep; and applying, by the system, a rule-based classification to the trigger to determine whether one or more parameters of a stimulation should be altered based on the biomarker.

DETAILED DESCRIPTION

The present disclosure relates to systems and methods to improve SDB. SDB can refer to several chronic conditions in which partial or complete cessation of breathing occurs at one or more times throughout the night, resulting in daytime sleepiness or fatigue that interferes with a patient's ability to function and reduces quality of life. OSA can refer to a type of SDB that is a breathing disorder that occurs primarily during sleep with consequences that may persist throughout the waking hours in the form of sleepiness. In some instances, despite an ongoing effort to breath, a patient experiencing OSA can experience a decrease or complete halt in airflow due to muscles relaxing during sleep, causing soft tissue in the back of the throat to collapse and block the airway. OSA can be characterized by periodic collapse of the upper airway during sleep with apneas, hypopneas, or a continuous or sustained reduction in ventilation and excessive daytime sleepiness, neurocognitive defects and depression.

The term "modulate" can refer to causing a change in neural activity and/or muscle activity, chemistry, and/or metabolism, such as an increase, decrease, or a change in a pattern of neuronal and/or muscle activity. For example, modulation may refer to either excitatory and/or inhibitory stimulation. "Stimulation" can refer to the activation and/or inhibition of neural activity and/or muscle activity and may also be referred to as "neuromuscular stimulation" or "neural stimulation". As such, stimulation can be excitatory or inhibitory. A "patient" includes a mammal, such as a human being. By "improving," or "treating" the patient's medical disorder is better after therapy than before therapy.

As used herein with respect to a described element, the terms "a," "an," and "the" include at least one or more of the described elements including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. The term "artificial intelligence" can refer to a computer's ability to correctly interpret/act on external data. The term "learning" can refer to the ability of artificial intelligence to improve from experience. The term "machine learning" can be used interchangeably with "learning." The term "rule-based classification" can refer to any suitable classification scheme, such as a classification scheme that makes use of IF-THEN rules for class prediction. The term "titration" can refer to a technique where parameters can be continually measured and updated. For example, titration can be a part of learning.

1. Overview

The present disclosure relates to improving SDB, such as OSA, through neural and/or muscular stimulation. Systems and methods described herein can provide the stimulation according to a closed loop stimulation algorithm. The closed loop stimulation algorithm can monitor physiological data (e.g., EMG data from the anterior lingual musculature, such as the genioglossus muscle), which can include characteristic signals that correlate to respiration, but also can correlate to sleep position, sleep state, and/or other physiological characteristics important for the treatment of OSA recorded by a sensor implanted in close proximity to an anterior lingual muscle such as the genioglossus muscle; identify a trigger within the physiological data that is identified as a biomarker for a condition related to sleep (e.g., inspiration); and applying a rule-based classification to the trigger to determine whether one or more parameters of the stimulation should be altered based on the biomarker. In some instances, the rule-based classification can include elements of artificial intelligence, like undergoing a type of learning so that the stimulation becomes better tailored to the specific patient.

As an example use, monitoring physiological or intrinsic EMG of the patient during sleep can be used to apply therapy in a closed-loop manner. EMG data from the anterior lingual muscles, specifically the genioglossus muscle, can be used to synchronize stimulation and with the patient's breathing pattern to open the patient's airway during certain phases of breathing that are associated with contraction of the genioglossus muscle, for example, By identifying inspiration/expiration via EMG signals of the genioglossus muscle, which innervates the tongue, the device can eliminate the requirement for a chest lead for sensing EMG activity, for example, of the diaphragm, or other methods associated with other OSA neurostimulation systems. A therapy signal, such as an electrical signal, can be delivered to the genioglossus muscle to treat an incidence of SDB of a patient in a closed-loop manner when the EMG data satisfies a trigger condition.

2. System

Figure 1:
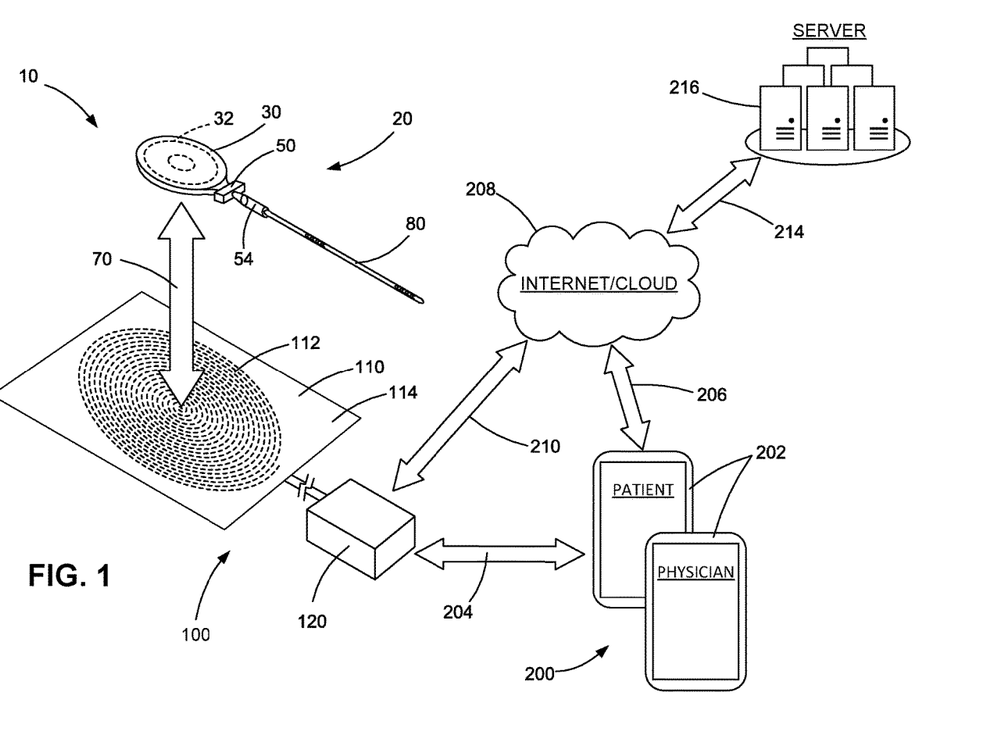
FIG. 1 is a diagram illustrating an example configuration of a stimulation system according to an aspect of the present disclosure.

In an aspect, the present disclosure can include a system that can be used to improve SDB through neuromodulation. Referring to FIG. 1, system 10 can include implantable stimulator 20 and external controller 100. Controller 100 can power stimulator 20 (shown in more detail in FIG. 2) through electromagnetic induction. Stimulator 20 can include power receiver 30 with antenna 32. Electrical current can be induced in antenna 32 when it is positioned above power mat 112 of controller 100, in an electric field produced by power transmit antenna 112. Antennas 112 and 32 can also facilitate communication between controller 100 and stimulator 20, respectively. This power/communication link between stimulator 20 and controller 100 is shown generally by the arrow 70 in FIG. 1.

System 10 can also include a user interface 200 in the form of a computer platform 202 running a custom application that enables communication with controller 100 wirelessly, as indicated generally by arrow 204. This can be done, for example, using Bluetooth or WiFi radio communication. In the example configuration of FIG. 1, computer platform 202 is a smartphone. The type of computer platform 202 could, however, vary. For example, the computer platform 202 can be a physician and/or patient platform. Each platform 202 can have an application or "app" installed thereon that is user specific, i.e., a patient app or a physician app. The patient app can allow the patient to execute certain commands necessary for controlling operation of stimulator 20, such as, for example, start/stop therapy, increase/decrease stimulation power, and select a stimulation program. In addition to the controls afforded the patient, the physician app can also allow the physician to modify stimulation settings, such as, but not limited to, pulse settings (patterns, duration, waveforms, etc.), stimulation frequency, amplitude settings, and electrode configurations, closed-loop and open loop control settings and tuning parameters.

As indicated generally by arrow 206, computer platform 202 can be connected (e.g., WiFi and/or LTE) to internet/cloud 208, which facilitates communication 214 with remote or cloud-based server 216. This allows for the transfer of data between server 216 and computer platform 202 via internet 208. Additionally, controller 100 itself can also be internet connected (e.g., WiFi), as shown at 210. This can also allow for the transfer of data between controller 100 and server 216 via internet 208.

As shown in FIG. 1 and described above, system 10 can be configured to provide various communication paths between the system components. For example, computer platform 202 being connected to controller 100 (see 204) and to internet 208 (see 206) can facilitate a communication path from remote server 216 (see 214) to stimulator 20 itself (see 70). A communication path between server 216 and stimulator 20 can also be established via WiFi link 210 of controller 100.

Additionally, recognizing that the physician may be remote from the patient, a physician communication path can be established via the internet connection 206 of the remotely located physician platform 202. Through this connection, remote physician platform 202 can communicate with server 216 through internet connection 206. Remote physician platform 202 can also communicate with controller 100, either via internet connection 210 (when enabled) or through patient controller 202.

The therapeutic approach implemented with system 10 can involve implanting only stimulator 20, leaving controller 100 as an external component to be used only during the application of therapy. To facilitate this, stimulator 20 can be configured to be powered by controller 100 through electromagnetic induction. In operation, power mat 110, operated by control unit 120, can be positioned external to the patient in the vicinity of stimulator 20 to position transmitting antenna 112 of the controller, located in the mat, close to receiving antenna 32 of the stimulator. Power mat 110 can be positioned on or sufficiently near the sleeping surface while the patient sleeps to maintain the position of the receiving antenna 32 within the target volume of the electromagnetic field generated by the transmit antenna 112.

Figure 2:
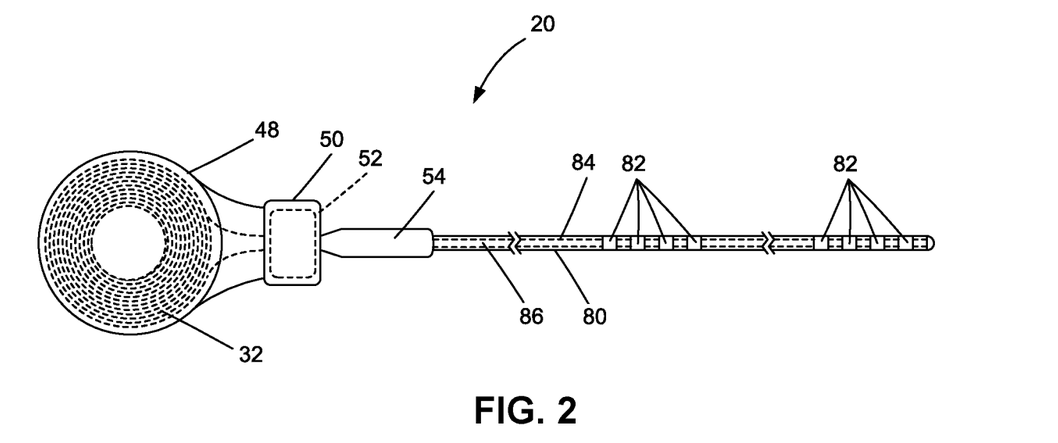
FIG. 2 is an illustration of an implantable stimulator portion of the system of FIG. 1.

Additionally, stimulator 20 can implement electromyography (EMG) electrodes for sensing neuromuscular responses to physiological activity of the patient during sleep as stated above. Such sensing electrodes can continuously monitor physiological intrinsic EMG signals from the anterior lingual musculature. For instance, EMG sensing electrodes can be configured to detect neuromuscular responses from the genioglossus muscle, which is innervated by the HGN.

In operation, sensed EMG responses from the genioglossus muscle can allow closed-loop operation of the stimulator 20 while eliminating the need for a chest lead. To facilitate real-time, closed-loop control, a control algorithm can be implemented locally on stimulator 20. This can be achieved, for example, by programming a control algorithm on an application-specific integrated circuit (ASIC) component of stimulator 20 although the control algorithm can be programmed on an external control device/component of the system. Operating in real-time, stimulator 20 can record data related to the stimulation session including, for example, stimulation settings, EMG responses, respiration, pulse, sleep state including different stages of REM and non-REM sleep, etc. After the sleep session, this recorded data can be uploaded to user interface 200 and to server 216. Also, the patient can be queried to use the interface 200 to log data regarding their perceived quality of sleep, which can also be uploaded to the server 216. Offline, the server 216 can execute a software application to evaluate the recorded data to determine whether settings and control parameters can be adjusted to further optimize the stimulation therapy. The software application can, for example, include artificial intelligence (AI) models that, learn from recorded therapy sessions, how certain adjustments affect the therapeutic outcome for the patient. In this manner, through AI learning, the model can provide patient-specific optimized therapy.

Figure 3:
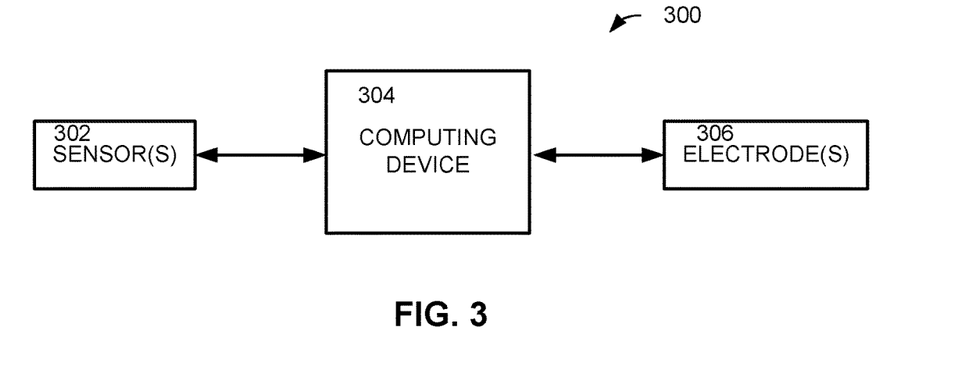
FIG. 3 is a block diagram of an example system that can provide neural stimulation according to a closed loop algorithm to treat sleep disordered breathing (SDB), which can be part of the system of FIG. 1.

With reference to FIG. 3, system 300 can be implemented within the system 10 and/or the stimulator 20 to provide stimulation to treat SDB according to open-loop control or closed-loop control. The system can include one or more sensors 302 (which can be implanted and/or external), a computing device 304 (which can be implanted and/or external, and may be part of another device like the controller), and one or more electrodes 306 (which can be implanted and/or external). The one or more sensors can be configured to record/detect physiological data (e.g. data originating from the patient's body) over time including changes therein. Exemplary physiological data can include phasic contraction of anterior lingual musculature, such as phasic genioglossus muscle contraction, underlying tonic activity of anterior lingual musculature, such as tonic activity of the genioglossus muscle, and combinations thereof. Phasic contraction of the genioglossus muscle can be indicative of inspiration, particularly the phasic activity that is layered within the underlying tonic tone of the genioglossus muscle. Changes in physiological data include changes in phasic contraction of anterior lingual musculature, such as phasic genioglossus muscle contraction, changes in underlying tonic activity of anterior lingual musculature, such as changes in tonic activity of the genioglossus muscle, and combinations thereof. For example, EMG signal changes can include changes in the frequency, amplitude, spike rate, or other features within the EMG signal. In particular, changes in phasic contraction of the genioglossus muscle can indicate a respiration or inspiration change and can be used to as a trigger for stimulation. Such physiological data and changes therein can be identified in recorded EMG signals, such as during different phases of respiration including inspiration. As such, one or more sensors 302 can include EMG sensors. The one or more sensors 302 can also include, for example, wireless or tethered sensors that measure, body temperature, movement, breath sounds (e.g. audio sensors), heart rate, pulse oximetry, eye motion, etc.

The computing device 304 can be configured to provide open-loop control and/or closed-loop stimulation to configure parameters for a stimulation. In other words, with respect to closed-loop stimulation, the computing device can be configured to track the patient's respiration (such as each breath of the patient) and stimulation can be applied during inspiration, for example. However, with respect to open-loop stimulation, stimulation can be applying without tracking specific physiological data, such as respiration or inspiration. However, even under such an "open loop" scenario, the computing device can still adjust stimulation and record data, to act on such information. For example, one way the computing device can act upon such information is that the computing device can configure parameters for stimulation to apply stimulation in an open loop fashion but can monitor the patient's respiration to know when to revert to applying stimulation on a breath to breath, close-loop fashion such that the system is always working in a close looped algorithm to assess data. Accordingly, adjustments to stimulation may be based on an input to the computing device 304, which may be based on one or more trends in physiological data recorded by the one or more sensors 302 over time. Treatment parameters of the system may be automatically adjusted in response to the physiological data. The physiological data can be stored over time and examined to change the treatment parameters; for example, the treatment data can be examined in real time to make a real time change to the treatment parameters.

The one or more electrodes 306 can deliver the stimulation configured according to the parameters. In some instances, the sensing component 302 and the electrode 306 can be the same structure or element. Advantageously, use of a single structure or element as the sensing component 302 and the electrode 306 reduces the invasive nature of the surgical procedure associated with implanting the system, while also reducing the number of foreign bodies introduced into a subject.

Figure 4:
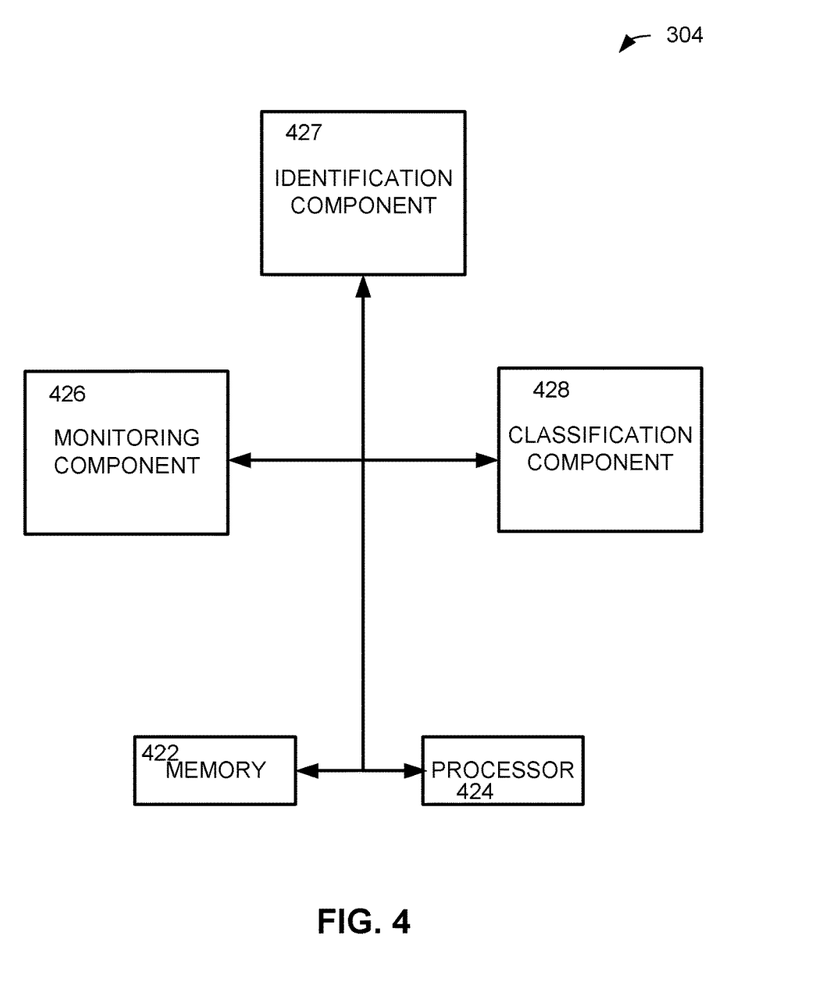
FIG. 4 is a block diagram of an example of the computing device shown in FIG. 3.
Figure 5:
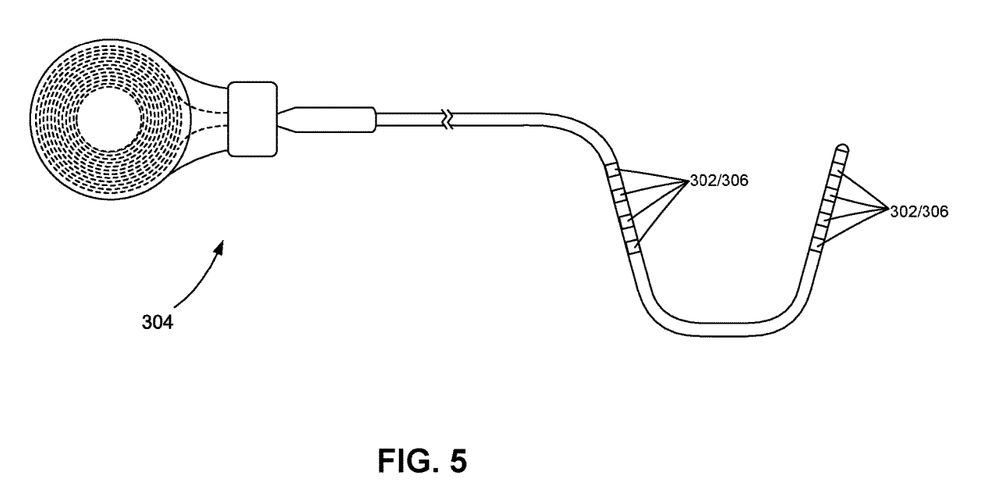
FIG. 5 is a diagram showing an exemplary implantable stimulator portion.

An example of the computing device 304 programmed to implement the closed-loop scenario is shown in FIG. 4. The computing device 304 can include a memory 422 (e.g., a non-transitory memory), a processor 424 (e.g., an integrated circuit, such as an application specific integrated circuit (ASIC)), or an ASIC comprising both a memory and a processor For example, the memory 422 can be a computer-usable or computer-readable medium that can contain or store the machine-readable instructions (which are, for example, a program) for use by or in connection with the instruction or execution of a system, apparatus or device (like the computing device 304) by the processor 424. The computer-usable or computer-readable medium can be, for example but not limited to, random access memory (RAM) including static or dynamic RAM, read-only memory (ROM), flash memory, an Erasable Programmable Read Only Memory (EPROM), floating point memory, or a combination thereofs including combinations thereof on the same ASIC. The processor 424, for example, can include one or more processing cores, processing units, or the like. The memory 422 can store machine readable instructions, while the processor 424 can access the memory 422 and execute the machine readable instructions (e.g., which can include one or more programs) and cause the computing device 304 to perform operations of a monitoring component 426, an identification component 427, and/or a classification component 428. The processor 424 can interpret the physiological information coming from the sensors, including decoding data, analyzing data, recognizing patterns, etc.

The monitoring component 426 can monitor the physiological data recorded by the sensor(s) 302. The identification component 427 can identify a trigger within the physiological data (e.g., related to respiration). For example, the monitoring component can monitor EMG waveform characteristics like spike rate, amplitude, and frequency, as well as phasic activity and tonic activity (again monitoring for changes in amplitude, frequency or other paramaters of the EMG). The identification component can identify the trigger during such monitoring (e.g. characteristic change in the EMG waveform). In one example, the trigger can be an associated change in the EMG, such as short term contraction of the genioglossus muscle indicating phasic genioglossus muscle activity or longer term changes in genioglossus muscle activity indicating the a change in underlying tonic tone of the genioglossus muscle seen over one or more parts or repetitions of the physiological data. The trigger can be identified as a biomarker for a condition related to sleep, such as a change in at least one parameter physiological data. In some instances, the biomarker can be inspiration. In other instances, the biomarker can be a body position. In other instances, the biomarker can be a stage in a sleep cycle (e.g., awake, non-REM sleep—stage 1 light sleep, stage 2 light sleep, stage 3 deep sleep, REM sleep, etc.). In some instances, motion detection and/or other biomarkers can be used to automatically turn the therapy on only once the patient has fallen asleep and to determine the parameters of stimulation to optimally maintain airway patency throughout the night (including adapting stimulation based on sleep stage and body position) without causing unnecessary discomfort or leading to arousal events to increase patient comfort and adherence to therapy. Stimulation can be ramped up as the patient moves from light to deep sleep or ramped during each stimulation phase such that the first pulse in a pulse train has less amplitude and/or pulse width than the last pulse in the pulse train. In some instances, stimulation will automatically shut off if the patient wakes up and re-initiate as they fall back to sleep.

The awake stage of the sleep cycle refers to a relaxation stage when the subject is first lying in bed or lying in bed trying to fall asleep again. Non-REM sleep has three stages and is a stage of sleep without rapid eye movement. The REM stage includes REM sleep, where eyes move rapidly from side to side behind closed eyelids, breathing becomes faster and irregular, heart rate and blood pressure increase to near waking levels, and arm and leg muscles become temporarily paralyzed.

Non-REM stage 1 refers to the changeover from wakefulness to sleep (lasting several minutes). During non-REM stage 1, a subject's heartbeat, breathing, and eye movements slow and muscles relax with occasional twitches. Non-REM stage 2, the longest of all the stages, is a period of light sleep before entering deeper sleep, where heartbeat and breathing slow, muscles relax even further, body temperature drops and eye movement stops. Non-REM stage 3 refers to the period of deep sleep needed to feel refreshed in the morning, where heartbeat and breathing slow to their lowest levels during sleep, muscles are relaxed, and it may be difficult to awaken.

The sleep state can be determined, for example, based on information in the physiological data (e.g., tonic genioglossus muscle activity as indicated on an EMG). Once the sleep state is recognized, the goal is to apply therapy in such a way to minimize patient discomfort and to also minimize potential stimulation related arousal events. This may include, reducing the amplitude of stimulation during stage 1 and stage 2 sleep, and increase amplitude during stage 3 and REM. This may also include ramping therapy over a longer period of time, meaning from zero to programmed output over a longer time period, during stage 1 and 2 sleep vs. stage 3 and REM sleep or ramping therapy within each pulse train, when applied during inspiration for example.

For example, if certain EMG activity is detected, like phasic changes in EMG activity that is indicative of inspiration during any phase of sleep, the system may deliver stimulation during the respiratory period of inspiration. The system can apply stimulation to the hypoglossal nerve, for example, using a particular set of electrodes, waveform, pulse width, frequency, intra-pulse interval and pulse ramp rate that provide therapeutic airway patency during inspiration. The system can stop stimulation during the exhalation period and can continue to monitor the physiological EMG, from the genioglossus muscle for example, throughout the inspiratory and exhalation periods of each breath. The system can adjust the stimulation parameters and/or the electrodes selected for stimulation as necessary to optimize the stimulation to provide the optimal airway patency, based on additional biomarkers including, sleep state, body position, or the like. The closed loop algorithms embedded within the stimulator or neuromodulation lead can continuously monitor and adjust therapy based on the physiological data, triggers and use rule based classification to determine when, how and for what period of time, to apply and adjust stimulation to provide optimal airway patency during sleep.

For example, if certain EMG activity, like tonic and phasic EMG activity drops or ceases during REM, the system may deliver a stimulation periodically based on predetermined physician programmed parameters, the system may rely on previous known patient specific parameters to apply stimulation, or the system may use a default periodic stimulation that is applied throughout REM sleep. The system can also monitor EMG through the REM period to determine when to stop using the periodic stimulation and when to re-initiate applying stimulation during each inspiratory event.

In some instances, the system may not turn on stimulation immediately when the stimulator is within the field from the transmit coil. In this case, the system can turn on and monitor an EMG signal, e.g., detecting tonic and phasic muscle activity, to understand the sleep stage. Once the system has determined the patient is sleeping, entering stage 1 of sleep or stage 2 of sleep, the system 10 can start to provide therapy in a physiological manner, e.g., starting to apply small amount of stimulation using a stimulus ramp during each stimulation period, such that unnecessary arousal events or discomfort is not caused during initial phases of sleep. In this configuration, the EMG may be monitored for several minutes or several hours to determine the state before the system initiates therapy. Many individuals with OSA also suffer from insomnia, in which the individual has trouble falling asleep, and in this case, a negative feedback loop can cause the patient additional anxiety, such that they are fearful that the therapy will turn on prior to when they fall asleep and as such are not relaxed enough to fall asleep. This can cause the individual to turn off therapy, or over time discontinue use of the therapy. A "smart" system that is able to recognize when patients are asleep and apply therapy such that it is physiological will increase therapy adherence and efficacy. Once the system recognizes non-REM stage 1, for example, the system can start to recognize non-REM stage 2, non-REM stage 3, REM sleep, or the like.

For example, the ASIC (an example of processor 424) can be configured to control a custom algorithm, which can control the therapy application. For example, the ASIC can be configured to run embedded digital logic that uses information gathered by an EMG sensor to decide when, for how long, and at what stimulation parameters to stimulate to provide the optimal therapy to the subject to control the volume of air capable of flowing through the upper airway, also known as airway patency. The embedded digital logic can sense EMG activity, which can be known to the algorithm to correspond with respiration, more specifically to inspiration and exhalation. The algorithm can decode the EMG activity to trigger stimulation of the anterior musculature and/or the hypoglossal nerve (including distal branches thereof) bilaterally, for example, to open the airway, such that the therapy is linked to each respiration, each inspiration and each exhalation, for example. Therapy is thus provided during each breath, specifically during inspiration, for example, all by using embedded correlative knowledge of the EMG features that correspond to respiration. The embedded logic can include knowledge of EMG features that are specific to body position, chin position, sleep state (e.g. REM, non-REM), movement, and other physiological parameters that can elucidate and optimize therapy. The algorithm can use adaptive learning to learn individual subject specific EMG features that correlate to the above physiological states during sleep to provide additional optimization that is subject specific. The adaptive learning can be done manually with physician input or may be done completely within the algorithm based on pre-determined limits and knowledge or can be done with the cloud database and the additional adaptive learning that the cloud software can use to analyze the data from each patient and each sleep session. The algorithm, while still based on respiratory information sensed through the EMG sensor, can also have different modes. In one mode, the algorithm can be running and can provide therapy breath to breath, specifically during inspiration; in another mode, the algorithm can be learning, looking for inputs from the EMG and also from the user (e.g. patient, physician, etc.); in another mode, the algorithm can provide more continuous control of the airway, providing periodic stimulation that can be sustained for periods of time. In another mode, the algorithm can be sensing EMG information, but not providing therapy breath to breath, instead waiting until a forthcoming collapse of the airway has been identified and reacting by providing therapy that prevents the collapse from occurring. The EMG information can include, the amplitude of the EMG, the frequency components of the EMG, spike sensing, envelop sensing, and other features that can be taken directly from the EMG signal to control the algorithm and provide biomarkers for respiration and for collapse of the airway. It is understood, that the algorithm may use any or all of these features throughout the sleep period and can switch between modes based on the EMG activity as sensed by the EMG sensor or the system may be hard programmed to only run one algorithm.

The system can apply therapy in a manner that is not causing discomfort and/or arousal events. As the patient moves through the stages over the course of the entire night, the system can continuously adapt to the sleep stage (and/or patient need). For example, the largest need for stimulation can be during deep sleep (non-REM stage 3) and REM, where discomfort and arousal are unlikely, so the system can apply more stimulation, since arousal and discomfort are unlikely during these stages. The amount of time the patient is spending in each stage of sleep can also be tracked, which is very useful for tracking outcomes, as most OSA patient do not enter into deep sleep often due to arousals.

The classification component 428 can apply a rule-based classification to the trigger to determine whether one or more stimulation parameters applied by one or more of the stimulating electrodes should be altered based on a biomarker related to sleep. As stated above, biomarkers include respiration phase (such as inspiration including periods within inspiration), sleep stage during one or more sleep cycles, and/or body position during sleep as indicated by an EMG or other sensor or sensed activity. Stimulation parameters, as stated above, include, for example, pulse width, amplitude, frequency, waveform shape, electrode position/configuration, or the like). Initial rules of the rule-based classification used by the algorithm can be set for the patient and/or set based on historical values for a population, historical values for a patient, and/or patient derived values. Subsequent rules of the algorithm can be learned and/or updated and/or personalized based on an artificial intelligence learning process.

Feedback related to the stimulation (e.g., after it is delivered) can be given to the computing device 304. The computing device 304 can receives the feedback and may change one or more stimulation parameters.

For example, the rules-based classification can employ one or more pattern recognition classifiers, each of which utilize the extracted features or a subset of the extracted features to determine an appropriate clinical parameter. Where multiple classifiers are used, an arbitration element can be utilized to provide a coherent result from the plurality of classifiers. Each classifier is trained on a plurality of training patterns representing various classes of interest. The training process of the given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, ensemble methods, rule based systems or artificial neural networks. The outcome class can represent a particular clinical parameter for the subject. From the provided feature vector, an outcome class is selected and a confidence in the selected result can be calculated. Results falling below a threshold confidence value can be rejected. For example, a support vector machine (SVM) classifier can process the training data (which can be related to any parameter being sensed, or the like) to produce functions representing boundaries in a feature space defined by the various attributes of interest. Similarly, an artificial neural network (ANN) classifier can process the training data (which can be related to any parameter being sensed, or the like) to determine a set of interconnection weights corresponding to the interconnections between nodes in its associated the neural network. A SVM classifier can utilize a plurality of functions, referred to as hyperplanes, to conceptually divide boundaries in the M-dimensional feature space, where each of the M dimensions represents one associated feature of the feature vector. The boundaries define a range of feature values associated with each class. Accordingly, an output class and an associated confidence value can be determined for a given input feature vector according to its position in feature space relative to the boundaries. A rule-based classifier applies a set of logical rules to the extracted features to select an output class. Generally, the rules are applied in order, with the logical result at each step influencing the analysis at later steps.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

In another example, the rule-based classification can employ a regression model configured to calculate a parameter representing a likelihood that the patient exhibits the biomarker. In yet another example, the rule-based classification can employ a sensitivity analysis using the model, such that a magnitude of the effect of one or more features on the at least one parameter can be determined and correlated to the biomarker.

An example closed-loop control scenario involves the one or more sensors 302 (implanted adjacent to an anterior lingual muscle, such as the genioglossus muscle) that can detect/record physiological data over time. The physiological data can include EMG data from the musculature of the anterior airway, which can include characteristic signals that correlate to respiration, but also can correlate to sleep position, sleep state, and/or other physiological characteristics important for the treatment of SDB. The computing device 304 can monitor the physiological data recorded by the one or more sensors 302 to identify a trigger within the physiological data. The trigger can be identified as a biomarker for a condition related to sleep (e.g., inspiration). A rule-based classification can be applied to the trigger to determine whether one or more parameters of the stimulation (e.g., delivered by one or more electrodes 306 or electrode contacts to the hypoglossal nerves) should be altered based on the biomarker.

Changes in voltages on the transmit receptor can be sensed, as well as on the power receiver and resulting changes in impedances to determine the position and movement of the power receptor within the magnetic field. In this aspect, the changes in voltage and impedance between the two coils of the power antenna can provide additional information to the system to inform the close loop algorithm and to inform additional refinement to the therapy. This type of position sensor may have additional usages beyond therapy optimization as it may provide additional data about sleep quality over time, as well as health related information. In addition, the impedance data between the coils can be correlated with activity, which can be used to also track wake vs. sleep cycles. These data along with EMG data, e.g. tonic EMG activity from the genioglossus muscle, can be used together to understand and learn wake vs. sleep throughout the period spent attempting to sleep (e.g., when the power receive coil is within the inductive field volume of the transmit coil).

Several wired or wireless input applications, including smart phone or tablet applications can also be used, wireless remote controls for example. These additional input applications can provide additional inputs to the system to adjust the therapy, adjust the closed loop algorithm, adjust stimulation outputs, adjust optimization or to adjust the algorithm mode as necessary. The input application can display electromyogram data for the user, allows the user to adjust the parameters that control the EMG collection, such as the input filters, trigger amplitudes, frequency ranges, etc.

An input application can also allow for automated therapy titration. In this mode, the application can run custom software that provides stimulation to a target site of the subject, such as a target nerve or target muscle and monitors the resulting evoked EMG activity of a muscle, such as an anterior lingual muscle, including the genioglossus muscle. The resulting EMG activity can correlate to the amount of airway opening desired (as inputted into the application) and thus can allow for automated therapeutic stimulation parameter settings and eliminate time consuming parameter adjustments during sleep Non-limiting example of stimulation parameter settings include stimulation pulse width, amplitude, frequency, electrode position/configuration and the like. In this aspect, the system can determine the therapeutic stimulation outputs and allows the subject/physician to fine tune as necessary. The subject or physician can rerun the automated parameter adjustment application at any time, and through the applications can be monitored remotely so that titration, programming can be done from the comfort of the subject's home.

The resultant evoked EMG signal can be continuously monitored and stimulation parameters needed to produce the required tongue motion for effective treatment can be determined, even if the response to a given set of stimulation parameters changes over time, effectively reducing the amount of testing required for initial programming as well as the need for ongoing follow-up testing. Also, issues with the therapy (e.g., stimulation according to certain stimulation parameter settings is not providing the tongue movement necessary to open the airway) can be identified and alerts can be generated for the patient and/or physician (this allows for quicker response and proactive management of the system).

Figure 6:
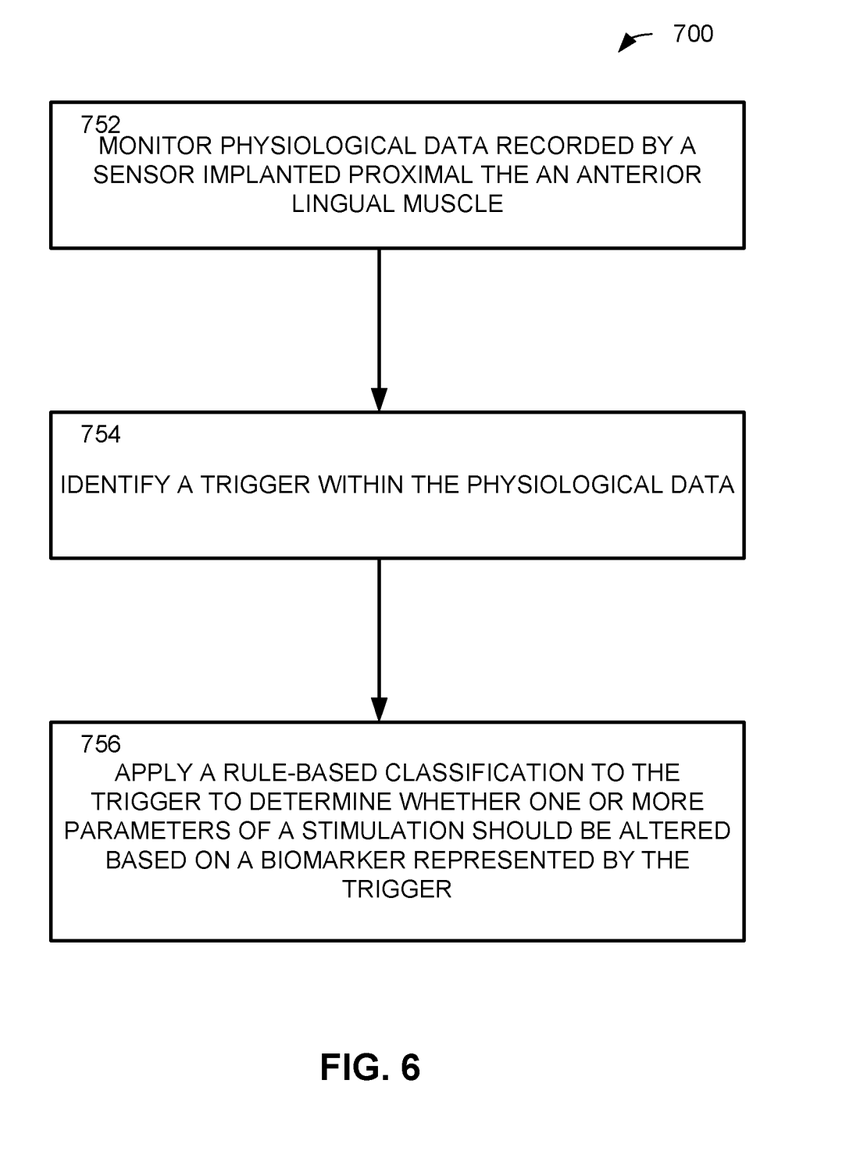
FIG. 6 is a process flow diagram of an example method for providing neural stimulation according to a closed loop algorithm to treat SDB, including OSA.

FIG. 6 shows an example of the components of FIG. 3 implemented within a stimulator device. The sensor(s) 302 and the electrode(s) 306 can be included in common electrode contacts. However, the sensor(s) and electrode(s) need not be within common electrode contacts and may be distinct and separate.

3. Methods

Another aspect of the present disclosure can include a method 700 (FIG. 7) for providing neural and/or muscular stimulation according to a closed loop algorithm to treat SDB. The method 700 can be executed by components of the systems shown in FIGS. 1-6, for example. Portions of the method 700 can be stored at least in part on a non-transitory memory and executed by a processor.

For purposes of simplicity, the method 700 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 700 and/or more than the illustrated aspects may be required to implement the method 700. Additionally, one or more aspects of the method 700 can be stored in one or more non-transitory memory devices and executed by one or more hardware processors.

At 752, physiological data (e.g., related to inspiration, sleep stage and/or body position as indicated by an EMG, for example) recorded by one or more sensors can be monitored. The one or more sensors can be implanted adjacent to the anterior lingual muscle, such as the genioglossus muscle, or in the plane between the genioglossus muscle and geniohyoid muscle, for example. At 754, a trigger can be identified within the physiological data. The trigger be a change in at least one parameter of the physiological data (e.g., indicative of inspiration during respiration, body position, and/or a stage in the sleep cycle as indicated by an EMG, for example).

At 756, a rule-based classification can be applied to the trigger to determine whether one or more parameters of the stimulation should be altered based on a biomarker represented by the trigger. A signal comprising configuration/setting information for the parameters can be sent to one or more electrodes located adjacent to the hypoglossal nerve, for example. The stimulation parameter(s) can be titrated based on the trigger to optimize airway muscle tone.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Furthermore, all references cited herein are incorporated by reference in their entirety.

What is claimed is:

1. A system comprising:
   a sensor implantable adjacent to an anterior lingual muscle in a subject and configured to record physiological data;
   a computing device comprising:
      a non-transitory memory storing instructions; and
      a processor to access the non-transitory memory and execute the instructions to at least:
         monitor the physiological data recorded by the sensor;
         identify a trigger within the physiological data, wherein the trigger comprises a detected biomarker; and
         apply a rule-based classification to the trigger to determine whether one or more parameters of a stimulation should be altered based on the trigger; and
   an electrode implantable adjacent to a hypoglossal nerve and configured to deliver the stimulation to the hypoglossal nerve during a sleep period and to alter the one or more parameters of the stimulation in response to a signal from the computing device,
   wherein the rule-based classification utilizes adaptive learning during the sleep period, or after the sleep period, or both during and after the sleep period to learn subject-specific biomarkers that correlate to sleep-related conditions in a manner personalized to the subject.

2. The system of claim 1, wherein the physiological data comprises inspiration, sleep stage, body position, or combinations thereof.

3. The system of claim 2, wherein the physiological data is obtained from EMG activity from the musculature of the anterior airway.

4. The system of claim 3, wherein the EMG activity comprises characteristic signals that correlate to respiration, sleep position, sleep state, or combinations thereof.

5. The system of claim 1, wherein the physiological data comprises phasic activity of the genioglossus muscle, tonic activity of the genioglossus muscle, or both.

6. The system of claim 1, wherein the sensor and the electrode are on a neuromodulation lead.

7. The system of claim 1, wherein the trigger comprises a change in at least one parameter of the physiological data.

8. The system of claim 7, wherein the physiological data is related to respiration and the at least one parameter is indicative of inspiration.

9. The system of claim 1, wherein at least one of the subject-specific biomarkers is related to a stage in a sleep cycle, wherein the stage in the sleep cycle is awake, non-REM stage 1 light sleep, non-REM stage 2 light sleep, non-REM stage 3 deep sleep, REM sleep, or combinations thereof.

10. The system of claim 1, wherein initial rules of an algorithm used by the rule-based classification are determined based on historical values for a population, historical values for a patient, and/or patient derived values.

11. The system of claim 1, wherein the trigger indicates a change in body position.

12. The system of claim 11, wherein the rule-based classification determines whether the one or more parameters should be altered based on the change in body position.

13. The system of claim 1, wherein at least one of the subject-specific biomarkers is related to an apneic event, a respiration rate, an inspiration, an expiration, a body position, and/or a chin position.

14. The system of claim 1, wherein the one or more parameters of the stimulation comprise at least one selected from the group consisting of: when to apply the stimulation, stimulation pulse width, stimulation amplitude, stimulation frequency, stimulation waveform shape, electrode position, and electrode configuration.

15. A method of improving sleep disordered breathing (SDB) in a subject comprising:
monitoring, by a system comprising a processor, physiological data recorded by a sensor implanted proximal to an anterior lingual muscle;
identifying, by the system, a trigger within the physiological data, wherein the trigger comprises a detected biomarker;
applying, by the system, a rule-based classification to the trigger to determine whether one or more parameters of a stimulation during a sleep period should be altered based on the trigger, wherein the rule-based classification utilizes adaptive learning during the sleep period, or after the sleep period, or both during and after the sleep period to learn subject-specific biomarkers that correlate to sleep-related conditions in a manner personalized to the subject.

16. The method of claim 15, further comprising sending, by the system, a signal comprising configuration or setting information for the parameters to an electrode located adjacent to the hypoglossal nerve.

17. The method of claim 15, wherein the trigger comprises a change in at least one parameter of the physiological data.

18. The method of claim 15, wherein the physiological data is related to respiration and the at least one parameter is indicative of inspiration.

19. The method of claim 15, wherein at least one of the subject-specific biomarkers is a stage in a sleep cycle of the patient, wherein the stage in the sleep cycle is awake, non-REM stage 1 light sleep, non-REM stage 2 light sleep, non-REM stage 3 deep sleep, REM sleep, or combinations thereof.

20. The method of claim 15, further comprising receiving, by the system, an indication of a change in body position, wherein the change in body position is used to identify the trigger.

21. The method of claim 15, further comprising titrating the stimulation parameters based on the trigger.

22. The method of claim 21, wherein the titrating optimizes airway muscle tone.

23. The method of claim 15, wherein the one or more parameters of the stimulation comprise at least one selected from the group consisting of: when to apply the stimulation, stimulation pulse width, stimulation amplitude, stimulation frequency, stimulation waveform shape, electrode position, and electrode configuration.

* * * * *

UNITED STATES PATENT AND TRADEMARK OFFICE
CERTIFICATE OF CORRECTION

PATENT NO. : 11,420,063 B2
APPLICATION NO. : 16/866488
DATED : August 23, 2022
INVENTOR(S) : Caparso et al.

It is certified that error appears in the above-identified patent and that said Letters Patent is hereby corrected as shown below:

On the Title Page

Item (72) Inventors, Line 2, delete "Louisville, KY (US)" insert -- Louisville, KY (US); Francis A. Papay, Cleveland, OH (US); Kelly Emerton, Santa Rosa, CA (US) --, therefor.

Signed and Sealed this
Twelfth Day of September, 2023

*Katherine Kelly Vidal*

Katherine Kelly Vidal
*Director of the United States Patent and Trademark Office*